United States Patent [19]

Yang

[11] 4,252,953
[45] Feb. 24, 1981

[54] ANTIBIOTIC CRYSTALLINE EPIMER

[75] Inventor: Kuo S. Yang, Greenwood, Ind.

[73] Assignee: Eli Lilly and Company, Indianapolis, Ind.

[21] Appl. No.: 35,037

[22] Filed: May 1, 1979

[51] Int. Cl.³ ............................................ C07D 265/12
[52] U.S. Cl. ................................ 544/105; 424/248.52
[58] Field of Search ................................. 544/105, 90; 424/248.52

[56] References Cited

U.S. PATENT DOCUMENTS

| | | | |
|---|---|---|---|
| 4,124,762 | 11/1978 | Haviv et al. | 544/21 X |
| 4,125,715 | 11/1978 | Haviv et al. | 544/21 X |
| 4,138,486 | 2/1979 | Narisada et al. | 424/248.52 |
| 4,148,997 | 4/1979 | Haviv et al. | 544/21 X |

OTHER PUBLICATIONS

Kim et al, Tetrahedron Letters, No. 5, pp. 409–412, (1978).
Lednicer et al, The Organic Chemistry of Drug Synthesis, pp. 418 to 420 and frontispage, John Wiley and Sons, NY, (1977).

*Primary Examiner*—John D. Randolph
*Attorney, Agent, or Firm*—William B. Scanlon; Arthur R. Whale

[57] ABSTRACT

Crystalline D-diammonium salt represented by the formula

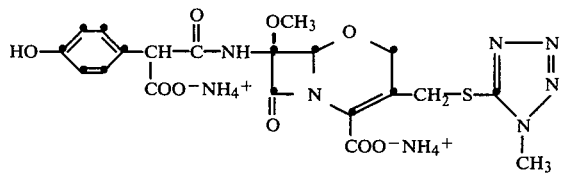

a useful pharmaceutical form of the corresponding antibiotic diacid is provided and processes for the preparation thereof.

9 Claims, No Drawings

ANTIBIOTIC CRYSTALLINE EPIMER

BACKGROUND OF THE INVENTION

This invention relates to a crystalline antibiotic salt. In particular, it relates to the oxa-β-lactam antibiotic diammonium salt represented by the formula I

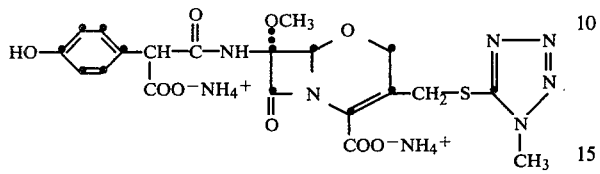

wherein the chiral center of the α-carboxy-p-hydroxyphenylacetyl side chain has the D-configuration. This invention also relates to a process for preparing the crystalline diammonium salt of the above formula as the D-epimer substantially free of the L-epimer.

U.S. Pat. No. 4,138,489, issued Feb. 6, 1979, describes the 1-oxa-β-lactam antibiotic diacid from which the diammonium salt of this invention is obtained. The patent teaches salts of the diacid including the sodium and potassium salts and amine salts such as the triethylammonium salt and the procaine salt. The salts of the diacid are forms of the antibiotic useful for parenteral administration of the antibiotic. As with most β-lactam antibiotics, such as the penicillins and the cephalosporins, which are used parenterally, a salt form of the antibiotic is most often the pharmaceutical form which is administered. The pharmaceutical salt form is desirably a stable crystalline salt compatible with and soluble in physiological fluids.

Although pharmaceutically acceptable salts of the oxa-β-lactam diacid are known, they have not been obtained in crystalline form with the desired stability. For example, the oxa-β-lactam disodium salt has been obtained as an amorphous solid. Copending application Ser. No. 32,840, filed on Apr. 24, 1979, describes the crystalline oxa-β-lactam sesquidisodium salt having the D-configuration which is a pharmaceutically acceptable form of the antibiotic.

DETAILED DESCRIPTION

The crystalline D-diammonium salt is obtained in the process of this invention, or when crystallized from aqueous organic solvents, as a tetrahydrate. The crystalline tetrahydrate salt has the following X-ray powder diffraction pattern obtained with copper/nickel radiation of 1.54 Å where "d" is the interplanar spacing and "I/I₁" is the relative intensity.

| d | I/I₁ × 100 |
|---|---|
| 9.60 | 1 |
| 8.79 | 50 |
| 8.11 | 50 |
| 7.25 | 10 |

| d | I/I₁ × 100 |
|---|---|
| 6.62 | 5 |
| 5.92 | 35 |
| 5.10 | 10 |
| 4.58 | 40 |
| 4.35 | 100 |
| 3.40 | 15 |
| 3.67 | 10 |
| 3.54 | 1 |
| 3.36 | 15 |
| 3.21 | 10 |
| 3.10 | 5 |
| 2.97 | 10 |
| 2.82 | 10 |
| 2.71 | 5 |
| 2.62 | 5 |
| 2.41 | 1 |
| 2.35 | 5 |
| 2.30 | 1 |
| 2.19 | 1 |
| 2.05 | 1 |

Electrometric titration of the diammonium salt in 66% dimethylformamide gave an initial pH of 7.38 and pKa values of about 5.0 (COO⁻), 6.2 (COO⁻), 9.5 (2NH₄⁺), and 12.9 (p hydroxy group).

The D-diammonium salt of the above formula is formally named 7β-[D-[carboxy(4-hydroxyphenyl)acetyl]-7α-methoxy-3-[[(1-methyl-1H-tetrazol-5-yl)thio]methyl]-8-oxo-5-oxa-1-azabicyclo[4.2.0]oct-2-ene-2-carboxylic acid diammonium salt. For convenience herein, the disalt is referred to as either the D-diammonium salt or the oxa-β-lactam D-diammonium salt.

The crystalline D-diammonium salt provided by this invention is a suitable pharmaceutical form which is stable at ordinary conditions of temperature and humidity. The salt can be stored in bulk form for later use, for example, in preparing unit dosage forms in ampoules.

The diammonium salt provided herein crystallizes in the D-epimeric form substantially free of the L-epimeric form. The D-epimer of the salt has shown higher antibacterial activity against some gram-negative bacteria, for instance *Escherichia coli*, than the D,L-form of the salt.

According to the process of this invention for preparing the crystalline D-diammonium salt, the oxa-β-lactam diacid of the formula

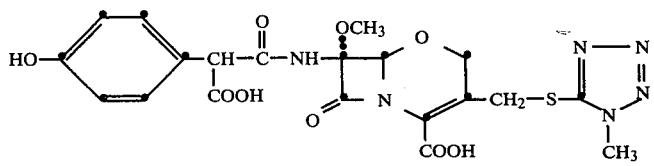

is dissolved in water and the solution is diluted with acetone in an amount of about 10 percent by volume. The pH of the solution is adjusted to between about pH 6 and about pH 7.5 with ammonium hydroxide and is then further diluted with acetone until the cloud point is reached. On standing the crystalline D-diammonium salt crystallizes and is separated from the mother liquor.

The diacid of the above formula used in the process can be in the L-epimeric form or any mixture of the D and L epimeric forms.

The concentration of the solution of the diacid in water is preferably about 10%; however, concentrations between about 5% and about 15% can also be used. Prior to addition of the ammonium hydroxide the water solution of the diacid is diluted with acetone, preferably to about 10% by volume, although more or less acetone dilution can be used.

Concentrated ammonium hydroxide is desirably used in the process since more dilute solutions of the base result in larger volumes of the crystallization solution necessitating the addition of more acetone. In large scale crystallizations it is desirable to avoid larger volumes where possible. Alternatively, a solution of ammonium hydroxide in acetone can be added to the aqueous solution of the diacid to adjust the pH. Solutions of about 1 N to about 1.5 N are preferable. Also, the desired pH can be achieved by passing ammonia into the aqueous diacid solution with cooling.

As mentioned above, the pH of the acetone diluted aqueous diacid solution is adjusted to about pH 6 to about pH 7.5 with the ammonium hydroxide. Preferably, the pH is adjusted to 6.5. After the ammonium hydroxide has been added to adjust the pH, the solution is further diluted with acetone until the solution becomes turbid. The crystalline diammonium salt crystallizes from the turbid solution as the D-epimer substantially free of the L-epimer. The crystals are harvested by filtration, centrifugation or other suitable separation method and are washed free of the mother liquor and are dried. Yields of the D-diammonium salt realized in the process are generally at least 85%.

The process is carried out conveniently at a temperature between about 15° C. and about 30° C. and preferably at about 25° C.

Under the conditions of pH and temperature of the process, the oxa-β-lactam acid and the diammonium salt of the diacid formed in solution undergo rapid epimerization at the chiral center in the α-carboxy p-hydroxyphenylacetyl side chain. When, for example, the starting diacid has the L-configuration, it or the diammonium salt in solution rapidly epimerizes to an equilibrium mixture of the D- and L-epimers. The equilibrium is upset by the precipitation of the crystalline D-diammonium salt as illustrated by the following diagram.

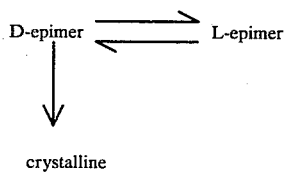

crystalline

D-diammonium salt

Accordingly, as the D-diammonium salt crystallizes as the least soluble epimer of the salt, the rapid epimerization in solution adjusts to the equilibrium to provide additional D-diammonium salt which crystallizes. The rapid epimerization described above is favored at the process temperatures of about 15° C. to about 30° C. and proceeds best at about 25° C. As the temperature is decreased the rate of epimerization decreases resulting in a slower crystallization and lower yields of the D-diammonium salt. Although decreased temperatures decrease the solubility of the D-diammonium salt, yet less becomes available in the crystallization solution because of the retarded rate of epimerization. Under the process conditions of this invention, high yields of the crystalline D-diammonium salt are obtained since rapid epimerization occurs while the D-epimer of the diammonium salt is substantially insoluble. At temperatures above the process temperatures, the rate of epimerization increases; however, the solubility of the D-epimer of the salt increases leading to lower yields of recoverable crystalline salt.

The D-epimer of the oxa-β-lactam diammonium salt is obtained substantially free of the L-epimer in the process of this invention. The term, "substantially free of the L-epimer" as used herein means at least 95% D-epimer. The percentage of the D-epimer in the crystalline diammonium salt product is determined by High Performance Liquid Chromatography (HPLC). One HPLC system which can be used to determine the percentages of the D-epimer and L-epimer is as follows:

Column: Water's Associates Bonopak C-18
Flow rate: 3 ml/min.
Solvent: 0.1 N ammonium acetate (100 parts) methyl alcohol (6 parts)
Sample solvent: pH 7.4 phosphate buffer
Sample concentration: 1 mg/ml
Sample volume: 15 microliters The D,L-oxa-β-lactam diacid used to prepare the salt of the invention can be separated by HPLC into enriched D-epimer and L-epimer for use in the process. Preferably the D,L-diacid is used.

In another aspect of this invention, crystalline D-diammonium salt of enhanced epimeric purity is obtained with non-crystalline diammonium salt having substantial L-epimeric form present. This aspect of the invention provides a crystallization process for the D-diammonium salt which comprises dissolving the diammonium salt in water and adding to the cloud point a water miscible organic solvent, such as ethyl alcohol, iso-propyl alcohol, n-propyl alcohol, and acetonitrile. On standing at the cloud point D-diammonium salt, substantially free of the L-diammonium salt, crystallizes from solution.

The crystallization process is carried out at a temperature between about 20° C. and about 35° C. It is a feature of the crystallization process that the D-epimer of the diammonium salt selectively crystallizes from the aqueous solution. The noncrystalline diammonium salt used in the crystallization can be a mixture of the D- and L-epimers which can be in various ratios. For example, the disalt can be enriched in the D-epimeric form by HPLC, or it can be approximately a 50:50 mixture of the two epimers.

The concentration of the water solution of the non-crystalline epimeric mixture of the diammonium salt is not critical, however, if too low larger volumes of the organic solvent are required and yields are generally lower. A convenient concentration is between about 0.1 g/ml to about 0.5 g/ml of water.

The D-diammonium salt crystallizes from the aqueous solution as the tetrahydrate. HPLC assay of the product obtained in the crystallization process shows the product contains at least 95% of the D-epimer compound.

The following examples further illustrate the invention described herein.

EXAMPLE 1

To a solution of 5 g of the 1-oxa-β-lactam diacid (40:60 D,L mixture) in 15 ml of 90:10, acetone: water, v:v, was added at room temperature with vigorous stirring a 1.4 N solution of ammonium hydroxide in acetone until the pH of the solution reached 6.5. Acetone was then added to the solution until the solution became cloudy. The solution was seeded with D-diammonium salt and allowed to stand while crystallization proceeded. The crystalline D-diammonium salt was filtered and washed with aqueous isopropyl alcohol (1:9, H₂O:iso-propyl alcohol, v:v) and was dried. The dried crystals weighed 4.5 g. The crystalline salt, assayed 97% D-epimer by HPLC.

EXAMPLE 2

Recrystallization of D-Diammonium Salt

Non-crystalline oxa-β-lactam diammonium salt, 100 mg in mainly the D-configuration (enriched in the D-epimer by HPLC using 0.1 N ammonium acetate buffer for elution) was dissolved in 0.5 ml of water. The solution was diluted slowly with iso-propyl alcohol until cloudy and was allowed to stand at room temperature for several hours. Small amounts of additional iso-propyl alcohol were added periodically to ensure complete crystallization. The crystals were filtered and washed with water:iso-propyl alcohol, 1:9, v:v and were dried under vacuum for several hours. The crystalline diammonium salt was 98% D-epimer as shown by HPLC.

The above procedure was reproduced on four more lots of non-crystalline diammonium salt having percent D-epimer contents of 98, 85, 82, and 76.

I claim:

1. The D-diammonium salt of the formula

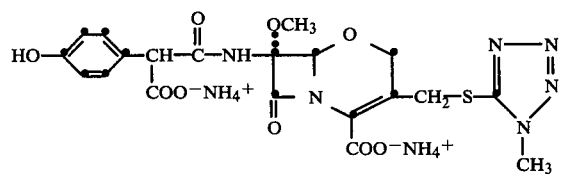

in crystalline form substantially free of the L-diammonium salt.

2. The process for preparing the D-diammonium salt of claim 1 which comprises (a) adding acetone to a water solution of the oxa-β-lactam diacid of the formula

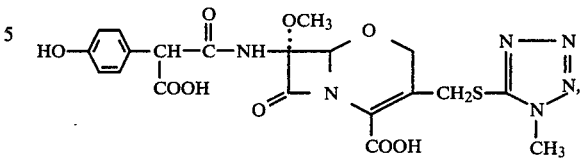

(b) adding to the aqueous acetone solution of said acid, at a temperature between about 15° and about 30° C., ammonium hydroxide until the pH of the solution is between about 6 and about 7.5, and (c) further diluting said solution with acetone to the cloud point, wherein said oxa-β-lactam diacid is in L-epimeric form or is a mixture of D- and L-epimeric forms.

3. The process of claim 2 wherein the pH is adjusted with 28% aqueous ammonium hydroxide.

4. The process of claim 2 wherein the pH is adjusted with a solution of ammonium hydroxide in acetone at a concentration of between about 1 N and about 1.5 N.

5. The process of claim 2 wherein the pH is adjusted to 6.5.

6. The process of claim 2 wherein the concentration of the water solution of the diacid is between about 5 percent and about 15 percent w/v.

7. The process for crystallizing the oxa-β-lactam D-diammonium salt which comprises diluting at a temperature between about 20° C. and about 30° C. a solution of a D,L-epimeric mixture of the diammonium salt in water with a water-miscible organic solvent until said solution reaches the cloud point.

8. The process of claim 7 wherein the D,L-epimeric mixture is in solution at a concentration between about 0.1 g/ml and about 0.5 g/ml of water.

9. The process of claim 7 wherein the water-miscible organic solvent is iso-propyl alcohol.